United States Patent
Chappa et al.

(10) Patent No.: US 11,628,466 B2
(45) Date of Patent: Apr. 18, 2023

(54) APPARATUS AND METHODS FOR COATING MEDICAL DEVICES

(71) Applicant: Surmodics, Inc., Eden Prairie, MN (US)

(72) Inventors: Ralph A. Chappa, Ham Lake, MN (US); Michael Militello, Eden Prairie, MN (US)

(73) Assignee: Surmodics, Inc., Eden Prairie, MN (US)

( * ) Notice: Subject to any disclaimer, the term of this patent is extended or adjusted under 35 U.S.C. 154(b) by 0 days.

(21) Appl. No.: 16/696,234

(22) Filed: Nov. 26, 2019

(65) Prior Publication Data

US 2020/0171531 A1    Jun. 4, 2020

Related U.S. Application Data

(60) Provisional application No. 62/772,673, filed on Nov. 29, 2018.

(51) Int. Cl.
*B05C 17/02*    (2006.01)
*B05C 17/03*    (2006.01)
*A61L 31/08*    (2006.01)

(52) U.S. Cl.
CPC ...... *B05C 17/0212* (2013.01); *B05C 17/0242* (2013.01); *B05C 17/0333* (2013.01); *A61L 31/08* (2013.01); *A61L 2420/02* (2013.01)

(58) Field of Classification Search
CPC ... B05C 17/0212; B05C 17/0242; B05C 5/00; B05D 1/26; A61M 25/10
See application file for complete search history.

(56) References Cited

U.S. PATENT DOCUMENTS 273,410 A    3/1883   Wadleigh et al.
554,114 A    2/1896   Evertz
(Continued)

FOREIGN PATENT DOCUMENTS

CA    2351016    12/2001
DE    3335502    3/1985
(Continued)

OTHER PUBLICATIONS

Braun, Dietrich "Plastics," Concise Encyclopedia of Polymer Science and Engineering, 1990 (pp. 461-464).
(Continued)

*Primary Examiner* — Dah-Wei D. Yuan
*Assistant Examiner* — Andrew J Bowman
(74) *Attorney, Agent, or Firm* — Pauly, DeVries Smith & Deffner LLC

(57) ABSTRACT

Embodiments of the invention include apparatus and methods for coating drug coated medical devices. In an embodiment, the invention includes a coating apparatus including a coating application unit. The coating application unit can include a fluid applicator having a lengthwise axis and a width. The fluid applicator can include a tip comprising a first face across the width of the fluid applicator. The first face of the fluid applicator can be oriented at an angle of from about 15 to about 75 degrees with respect to the lengthwise axis of the fluid applicator. The fluid applicator can define a second face intersecting the first face. The coating apparatus can further include a rotation mechanism and an axial motion mechanism. Other embodiments are also included herein.

14 Claims, 7 Drawing Sheets

(56) References Cited

U.S. PATENT DOCUMENTS

| | | |
|---|---|---|
| 1,281,672 A | 10/1918 | Schorn |
| 1,866,100 A | 7/1932 | Hach |
| 2,253,019 A | 8/1941 | Crepeau |
| 2,329,438 A | 9/1943 | Fiedler |
| 2,330,880 A | 10/1943 | Gladfelter et al. |
| 2,335,116 A | 11/1943 | Hansen |
| 2,398,506 A | 4/1946 | Rogers |
| 2,493,787 A | 1/1950 | Torretti |
| 2,781,280 A | 2/1957 | Miller |
| 2,821,158 A | 1/1958 | Brown et al. |
| 2,881,461 A | 4/1959 | Parker |
| 3,198,170 A | 8/1965 | Toshio |
| 3,318,281 A | 5/1967 | Plegat |
| 3,348,964 A | 10/1967 | Good et al. |
| 3,416,530 A | 12/1968 | Ness |
| 3,502,494 A | 3/1970 | Ishiwata et al. |
| 3,625,214 A | 12/1971 | Higuchi |
| 3,645,773 A | 2/1972 | Herzhoff et al. |
| 3,663,292 A | 5/1972 | Herzhoff et al. |
| 3,669,917 A | 6/1972 | Ando et al. |
| 3,699,917 A | 10/1972 | Deverse et al. |
| 3,702,739 A | 11/1972 | Rentfrow |
| 3,723,120 A | 3/1973 | Hummel et al. |
| 3,736,199 A | 5/1973 | Mason |
| 3,837,805 A | 9/1974 | Boucher |
| 3,935,896 A | 2/1976 | Tegtmeier et al. |
| 3,936,549 A | 2/1976 | Kohler et al. |
| 3,963,069 A | 6/1976 | Marti et al. |
| 3,966,120 A | 6/1976 | Furgalus et al. |
| 4,000,745 A | 1/1977 | Goldberg |
| 4,016,306 A | 4/1977 | Miyagawa et al. |
| 4,051,805 A | 10/1977 | Waldrum |
| 4,060,116 A | 11/1977 | Frailly |
| 4,069,307 A | 1/1978 | Higuchi et al. |
| 4,073,335 A | 2/1978 | Fort et al. |
| 4,075,975 A | 2/1978 | Oswald |
| 4,082,870 A | 4/1978 | Yenni |
| 4,144,317 A | 3/1979 | Higuchi et al. |
| 4,146,036 A | 3/1979 | Dutcher et al. |
| 4,148,934 A | 4/1979 | Baker |
| 4,153,201 A | 5/1979 | Berger et al. |
| 4,174,678 A | 11/1979 | Van Den Bergh |
| 4,195,637 A | 4/1980 | Gruntzig et al. |
| 4,196,231 A | 4/1980 | Hubers |
| 4,197,338 A | 4/1980 | Perna |
| 4,206,756 A | 6/1980 | Grossan |
| 4,209,019 A | 6/1980 | Dutcher et al. |
| 4,240,373 A | 12/1980 | Anger |
| 4,257,343 A | 3/1981 | Kullander |
| 4,289,089 A | 9/1981 | Tacke et al. |
| 4,292,965 A | 10/1981 | Nash |
| 4,300,557 A | 11/1981 | Refojo et al. |
| 4,301,968 A | 11/1981 | Berger et al. |
| 4,304,765 A | 12/1981 | Shell et al. |
| 4,337,896 A | 7/1982 | Berger et al. |
| 4,352,459 A | 10/1982 | Berger et al. |
| 4,364,879 A | 12/1982 | Gut et al. |
| 4,375,820 A | 3/1983 | Vinarcsik et al. |
| 4,415,654 A | 11/1983 | Pohl |
| 4,475,972 A | 10/1984 | Wong |
| 4,503,802 A | 3/1985 | Keller et al. |
| 4,541,564 A | 9/1985 | Berger et al. |
| 4,544,626 A | 10/1985 | Sullivan |
| 4,567,934 A | 2/1986 | Nakao et al. |
| 4,572,451 A | 2/1986 | Ikeda et al. |
| 4,575,330 A | 3/1986 | Hull |
| 4,603,058 A | 7/1986 | Adams |
| 4,616,593 A | 10/1986 | Kawamura et al. |
| 4,622,917 A | 11/1986 | Schramm |
| 4,638,045 A | 1/1987 | Kohn et al. |
| 4,655,393 A | 4/1987 | Berger |
| 4,678,466 A | 7/1987 | Rosenwald |
| 4,723,708 A | 2/1988 | Berger et al. |
| 4,743,252 A | 5/1988 | Martin, Jr. et al. |
| 4,764,377 A | 8/1988 | Goodson |
| 4,819,661 A | 4/1989 | Heil et al. |
| 4,824,017 A | 4/1989 | Mansfield |
| 4,853,224 A | 8/1989 | Wong |
| 4,863,457 A | 9/1989 | Lee et al. |
| 4,892,736 A | 1/1990 | Goodson |
| 4,927,741 A | 5/1990 | Garth et al. |
| 4,953,564 A | 9/1990 | Berthelsen |
| 4,959,217 A | 9/1990 | Sanders et al. |
| 4,971,895 A | 11/1990 | Sullivan |
| 4,972,848 A | 11/1990 | Di Domenico et al. |
| 4,978,067 A | 12/1990 | Berger et al. |
| 4,988,883 A | 1/1991 | Oppawsky |
| 4,997,652 A | 3/1991 | Wong et al. |
| 5,002,067 A | 3/1991 | Berthelsen et al. |
| 5,002,582 A | 3/1991 | Guire et al. |
| 5,003,992 A | 4/1991 | Holleman et al. |
| 5,036,634 A | 8/1991 | Lessard et al. |
| 5,041,089 A | 8/1991 | Mueller et al. |
| 5,049,404 A | 9/1991 | Kisler et al. |
| 5,069,940 A | 12/1991 | Wenrick |
| 5,071,337 A | 12/1991 | Heller et al. |
| 5,076,285 A | 12/1991 | Hess et al. |
| 5,076,974 A | 12/1991 | Modrek et al. |
| 5,087,246 A | 2/1992 | Smith |
| 5,090,084 A | 2/1992 | De |
| 5,098,443 A | 3/1992 | Parel et al. |
| 5,102,402 A | 4/1992 | Dror et al. |
| 5,114,719 A | 5/1992 | Sabel et al. |
| 5,120,312 A | 6/1992 | Wigness et al. |
| 5,164,188 A | 11/1992 | Wong |
| 5,183,509 A | 2/1993 | Brown et al. |
| 5,207,343 A | 5/1993 | Bogadi |
| 5,219,120 A | 6/1993 | Ehrenberg et al. |
| 5,219,690 A | 6/1993 | Hammond |
| 5,221,698 A | 6/1993 | Amiden et al. |
| 5,229,128 A | 7/1993 | Haddad et al. |
| 5,246,867 A | 9/1993 | Maliwal et al. |
| 5,248,752 A | 9/1993 | Argyropoulos et al. |
| 5,254,164 A | 10/1993 | Masahumi |
| 5,255,693 A | 10/1993 | Dutcher et al. |
| 5,300,108 A | 4/1994 | Rebell et al. |
| 5,300,114 A | 4/1994 | Gwon |
| 5,304,121 A | 4/1994 | Sahatjian |
| 5,310,559 A | 5/1994 | Shah et al. |
| 5,314,419 A | 5/1994 | Pelling et al. |
| 5,318,587 A | 6/1994 | Davey |
| 5,324,325 A | 6/1994 | Moaddeb |
| 5,344,298 A | 9/1994 | Hull |
| 5,364,343 A | 11/1994 | Apolet et al. |
| 5,372,577 A | 12/1994 | Ungerleider |
| 5,378,475 A | 1/1995 | Smith et al. |
| 5,382,234 A | 1/1995 | Cornelius et al. |
| 5,385,148 A | 1/1995 | Lesh et al. |
| 5,387,247 A | 2/1995 | Vallana et al. |
| 5,395,618 A | 3/1995 | Darougar et al. |
| 5,405,376 A | 4/1995 | Mulier et al. |
| 5,405,631 A | 4/1995 | Rosenthal |
| 5,410,773 A | 5/1995 | Forkner |
| 5,413,638 A | 5/1995 | Bernstein, Jr. et al. |
| 5,414,075 A | 5/1995 | Swan et al. |
| 5,421,979 A | 6/1995 | Stevenson |
| 5,423,777 A | 6/1995 | Tajiri et al. |
| 5,431,649 A | 7/1995 | Mulier et al. |
| 5,437,656 A | 8/1995 | Shikani et al. |
| 5,443,505 A | 8/1995 | Wong et al. |
| 5,447,724 A | 9/1995 | Helmus et al. |
| 5,449,382 A | 9/1995 | Dayton |
| 5,464,650 A | 11/1995 | Berg et al. |
| 5,466,233 A | 11/1995 | Weiner et al. |
| 5,472,436 A | 12/1995 | Fremstad |
| 5,476,511 A | 12/1995 | Gwon et al. |
| 5,501,735 A | 3/1996 | Pender |
| 5,501,856 A | 3/1996 | Ohtori et al. |
| 5,512,055 A | 4/1996 | Domb et al. |
| 5,525,348 A | 6/1996 | Whitbourne et al. |
| 5,527,389 A | 6/1996 | Rosenblum et al. |
| 5,545,208 A | 8/1996 | Wolff et al. |
| 5,556,633 A | 9/1996 | Haddad et al. |
| 5,571,089 A | 11/1996 | Crocker |

(56) References Cited

U.S. PATENT DOCUMENTS

| | | |
|---|---|---|
| 5,578,075 A | 11/1996 | Dayton |
| 5,582,616 A | 12/1996 | Bolduc et al. |
| 5,591,227 A | 1/1997 | Dinh et al. |
| 5,605,696 A | 2/1997 | Eury et al. |
| 5,609,629 A | 3/1997 | Fearnot et al. |
| 5,618,568 A | 4/1997 | Seckora et al. |
| 5,624,411 A | 4/1997 | Tuch |
| 5,624,975 A | 4/1997 | Valencia |
| 5,626,919 A | 5/1997 | Chapman et al. |
| 5,630,879 A | 5/1997 | Eichmann et al. |
| 5,637,113 A | 6/1997 | Tartaglia et al. |
| 5,637,460 A | 6/1997 | Swan et al. |
| 5,643,362 A | 7/1997 | Garves |
| 5,645,592 A | 7/1997 | Nicolais et al. |
| 5,651,986 A | 7/1997 | Brem |
| 5,656,332 A | 8/1997 | Saito et al. |
| 5,658,387 A | 8/1997 | Reardon et al. |
| 5,673,473 A | 10/1997 | Johnson et al. |
| 5,679,400 A | 10/1997 | Tuch |
| 5,714,360 A | 2/1998 | Swan et al. |
| 5,725,493 A | 3/1998 | Avery et al. |
| 5,743,964 A | 4/1998 | Pankake |
| 5,766,242 A | 6/1998 | Wong et al. |
| 5,773,019 A | 6/1998 | Ashton et al. |
| 5,776,101 A | 7/1998 | Goy |
| 5,788,772 A | 8/1998 | Kunieda et al. |
| 5,807,331 A | 9/1998 | Den Heijer et al. |
| 5,807,395 A | 9/1998 | Mulier et al. |
| 5,810,836 A | 9/1998 | Hussein et al. |
| 5,824,072 A | 10/1998 | Wong |
| 5,830,173 A | 11/1998 | Avery et al. |
| 5,833,715 A | 11/1998 | Vachon et al. |
| 5,833,891 A | 11/1998 | Subramaniam et al. |
| 5,837,008 A | 11/1998 | Berg et al. |
| 5,837,088 A | 11/1998 | Palmgren et al. |
| 5,837,313 A | 11/1998 | Ding et al. |
| 5,849,359 A | 12/1998 | Burns et al. |
| 5,858,435 A | 1/1999 | Gallo |
| 5,868,697 A | 2/1999 | Richter et al. |
| 5,877,224 A | 3/1999 | Brocchini et al. |
| 5,882,336 A | 3/1999 | Janacek |
| 5,882,405 A | 3/1999 | Kish et al. |
| 5,886,026 A | 3/1999 | Hunter et al. |
| 5,897,911 A | 4/1999 | Loeffler |
| 5,904,144 A | 5/1999 | Hammage et al. |
| 5,913,653 A | 6/1999 | Kempf |
| 5,921,982 A | 7/1999 | Lesh et al. |
| 5,925,885 A | 7/1999 | Clark et al. |
| 5,928,662 A | 7/1999 | Phillips |
| 5,972,027 A | 10/1999 | Johnson |
| 5,972,369 A | 10/1999 | Roorda et al. |
| 5,976,256 A | 11/1999 | Kawano |
| 5,980,972 A | 11/1999 | Ding |
| 5,989,579 A | 11/1999 | Darougar et al. |
| 5,992,568 A | 11/1999 | Craig et al. |
| 5,997,517 A | 12/1999 | Whitbourne |
| 6,001,386 A | 12/1999 | Ashton et al. |
| 6,001,425 A | 12/1999 | Stash et al. |
| 6,019,784 A | 2/2000 | Hines |
| 6,033,582 A | 3/2000 | Lee et al. |
| 6,053,924 A | 4/2000 | Hussein |
| 6,056,998 A | 5/2000 | Fujimoto |
| 6,070,697 A | 6/2000 | Millard |
| 6,074,661 A | 6/2000 | Olejnik et al. |
| 6,091,978 A | 7/2000 | Johnson et al. |
| 6,094,887 A | 8/2000 | Swank et al. |
| 6,096,070 A | 8/2000 | Ragheb et al. |
| 6,099,562 A | 8/2000 | Ding et al. |
| 6,102,887 A | 8/2000 | Altman |
| 6,110,483 A | 8/2000 | Whitbourne et al. |
| 6,117,456 A | 9/2000 | Lee et al. |
| 6,120,536 A | 9/2000 | Ding et al. |
| 6,129,933 A | 10/2000 | Oshlack et al. |
| 6,143,037 A | 11/2000 | Goldstein et al. |
| 6,153,252 A | 11/2000 | Hossainy et al. |
| 6,156,373 A | 12/2000 | Zhong et al. |
| 6,156,526 A | 12/2000 | Newman |
| 6,165,526 A | 12/2000 | Newman et al. |
| 6,177,095 B1 | 1/2001 | Sawhney et al. |
| 6,187,370 B1 | 2/2001 | Dinh et al. |
| 6,190,077 B1 | 2/2001 | Newson et al. |
| 6,197,324 B1 | 3/2001 | Crittenden |
| 6,203,551 B1 | 3/2001 | Wu |
| 6,203,556 B1 | 3/2001 | Evans et al. |
| 6,203,732 B1 | 3/2001 | Clubb et al. |
| 6,207,337 B1 | 3/2001 | Swain |
| 6,212,434 B1 | 4/2001 | Scheiner et al. |
| 6,214,008 B1 | 4/2001 | Illi |
| 6,214,115 B1 | 4/2001 | Taylor et al. |
| 6,214,901 B1 | 4/2001 | Chudzik et al. |
| 6,217,895 B1 | 4/2001 | Guo et al. |
| 6,218,016 B1 | 4/2001 | Tedeschi |
| 6,245,089 B1 | 6/2001 | Daniel et al. |
| 6,245,099 B1 | 6/2001 | Edwin et al. |
| 6,248,112 B1 | 6/2001 | Gambale et al. |
| 6,251,090 B1 | 6/2001 | Avery et al. |
| 6,251,136 B1 | 6/2001 | Guruwaiya et al. |
| 6,251,418 B1 | 6/2001 | Ahern et al. |
| 6,254,921 B1 | 7/2001 | Chappa et al. |
| 6,278,018 B1 | 8/2001 | Swan |
| 6,279,505 B1 | 8/2001 | Plester et al. |
| 6,287,285 B1 | 9/2001 | Michal et al. |
| 6,290,728 B1 | 9/2001 | Phelps et al. |
| 6,298,272 B1 | 10/2001 | Peterfeso et al. |
| 6,303,148 B1 | 10/2001 | Hennink et al. |
| 6,306,125 B1 | 10/2001 | Parker et al. |
| 6,306,426 B1 | 10/2001 | Olejnik et al. |
| 6,309,370 B1 | 10/2001 | Haim et al. |
| 6,322,847 B1 | 11/2001 | Zhong et al. |
| RE37,463 E | 12/2001 | Altman |
| 6,331,313 B1 | 12/2001 | Wong et al. |
| 6,333,595 B1 | 12/2001 | Horikawa et al. |
| 6,344,035 B1 | 2/2002 | Chudzik et al. |
| 6,345,630 B2 | 2/2002 | Fishkin et al. |
| 6,358,247 B1 | 3/2002 | Altman et al. |
| 6,358,556 B1 | 3/2002 | Ding et al. |
| 6,360,129 B1 | 3/2002 | Ley et al. |
| 6,368,658 B1 | 4/2002 | Schwarz et al. |
| 6,375,972 B1 | 4/2002 | Guo et al. |
| 6,394,995 B1 | 5/2002 | Solar et al. |
| 6,395,326 B1 | 5/2002 | Castro et al. |
| 6,399,144 B2 | 6/2002 | Dinh et al. |
| 6,399,655 B1 | 6/2002 | De et al. |
| 6,399,704 B1 | 6/2002 | Laurin et al. |
| 6,406,754 B2 | 6/2002 | Chappa et al. |
| 6,431,770 B1 | 8/2002 | Kurematsu et al. |
| 6,435,959 B1 | 8/2002 | Skrmetta |
| 6,451,373 B1 | 9/2002 | Hossainy et al. |
| 6,478,776 B1 | 11/2002 | Roseman et al. |
| 6,497,691 B1 | 12/2002 | Bevins et al. |
| 6,501,994 B1 | 12/2002 | Janke et al. |
| 6,505,082 B1 | 1/2003 | Scheiner et al. |
| 6,506,411 B2 | 1/2003 | Hunter et al. |
| 6,506,437 B1 | 1/2003 | Harish et al. |
| 6,517,515 B1 | 2/2003 | Eidenschink |
| 6,517,889 B1 | 2/2003 | Jayaraman |
| 6,521,299 B1 | 2/2003 | Dessauer |
| 6,527,863 B1 | 3/2003 | Pacetti et al. |
| 6,544,544 B2 | 4/2003 | Hunter et al. |
| 6,544,582 B1 | 4/2003 | Yoe |
| 6,547,787 B1 | 4/2003 | Altman et al. |
| 6,548,078 B2 | 4/2003 | Guo et al. |
| 6,555,157 B1 | 4/2003 | Hossainy |
| 6,559,560 B1 | 5/2003 | Jin et al. |
| 6,562,051 B1 | 5/2003 | Bolduc et al. |
| 6,562,136 B1 | 5/2003 | Chappa et al. |
| 6,565,659 B1 | 5/2003 | Pacetti et al. |
| 6,572,644 B1 | 6/2003 | Moein |
| 6,585,764 B2 | 7/2003 | Wright et al. |
| 6,595,958 B1 | 7/2003 | Mickley |
| 6,599,560 B1 | 7/2003 | Daggett et al. |
| 6,605,154 B1 | 8/2003 | Villareal |
| 6,607,598 B2 | 8/2003 | Schwarz et al. |
| 6,613,017 B1 | 9/2003 | Mickley |

(56) References Cited

U.S. PATENT DOCUMENTS

| | | |
|---|---|---|
| 6,616,765 B1 | 9/2003 | Castro et al. |
| 6,623,504 B2 | 9/2003 | Vrba et al. |
| 6,653,426 B2 | 11/2003 | Alvarado et al. |
| 6,656,529 B1 | 12/2003 | Pankake |
| 6,669,980 B2 | 12/2003 | Hansen |
| 6,669,994 B2 | 12/2003 | Swan et al. |
| 6,673,154 B1 | 1/2004 | Pacetti et al. |
| 6,676,987 B2 | 1/2004 | Zhong et al. |
| 6,695,920 B1 | 2/2004 | Pacetti et al. |
| 6,706,023 B1 | 3/2004 | Huttner et al. |
| 6,709,514 B1 | 3/2004 | Hossainy |
| 6,709,712 B2 | 3/2004 | Chappa et al. |
| 6,713,081 B2 | 3/2004 | Robinson et al. |
| 6,716,081 B2 | 4/2004 | Kim et al. |
| 6,716,196 B2 | 4/2004 | Lesh et al. |
| 6,719,750 B2 | 4/2004 | Varner et al. |
| 6,719,805 B1 | 4/2004 | Ahern |
| 6,723,373 B1 | 4/2004 | Narayanan et al. |
| 6,725,901 B1 | 4/2004 | Kramer et al. |
| 6,726,918 B1 | 4/2004 | Wong et al. |
| 6,743,233 B1 | 6/2004 | Baldwin et al. |
| 6,743,462 B1 | 6/2004 | Pacetti |
| 6,743,463 B2 | 6/2004 | Weber et al. |
| 6,752,959 B2 | 6/2004 | Smith et al. |
| 6,764,470 B2 | 7/2004 | Dimick |
| 6,783,793 B1 | 8/2004 | Hossainy et al. |
| 6,803,070 B2 | 10/2004 | Weber |
| 6,818,063 B1 | 11/2004 | Kerrigan |
| 6,896,842 B1 | 5/2005 | Hamilton et al. |
| 6,941,632 B1 | 9/2005 | Mead et al. |
| 6,981,982 B2 | 1/2006 | Armstrong et al. |
| 7,010,933 B2 | 3/2006 | Ishitomi et al. |
| 7,041,174 B2 | 5/2006 | Carlson et al. |
| 7,045,015 B2 | 5/2006 | Renn et al. |
| 7,077,848 B1 | 7/2006 | De Juan, Jr. et al. |
| 7,077,910 B2 | 7/2006 | Chappa et al. |
| 7,087,658 B2 | 8/2006 | Swan et al. |
| 7,090,421 B1 | 8/2006 | Mead et al. |
| 7,105,350 B2 | 9/2006 | Foster et al. |
| 7,125,577 B2 | 10/2006 | Chappa |
| 7,163,523 B1 | 1/2007 | Devens, Jr. et al. |
| 7,186,374 B2 | 3/2007 | Zelina et al. |
| 7,192,484 B2 | 3/2007 | Chappa et al. |
| 7,198,675 B2 | 4/2007 | Fox et al. |
| 7,335,314 B2 | 2/2008 | Wu |
| 7,563,324 B1 | 7/2009 | Chen et al. |
| 7,611,532 B2 | 11/2009 | Bates et al. |
| 7,638,156 B1 | 12/2009 | Kokish et al. |
| 7,669,548 B2 | 3/2010 | Chappa |
| 7,743,727 B2 | 6/2010 | Shekalim |
| 7,806,612 B1 | 10/2010 | Wangler |
| 7,883,749 B2 | 2/2011 | Carlson |
| 7,958,840 B2 | 6/2011 | Chappa |
| 8,003,156 B2 | 8/2011 | Van Sciver |
| 8,166,909 B2 | 5/2012 | Chappa |
| 8,171,595 B1 | 5/2012 | Umhoefer, Jr. et al. |
| 8,246,974 B2 | 8/2012 | Chappa |
| 8,282,981 B2 | 10/2012 | Andreacchi et al. |
| 8,318,263 B2 | 11/2012 | Carlson et al. |
| D676,975 S | 2/2013 | Bickford |
| 8,632,837 B2 | 1/2014 | Gong et al. |
| 8,844,543 B2 | 9/2014 | Bickford et al. |
| 8,889,760 B2 | 11/2014 | Kurdyumov et al. |
| 8,961,054 B2 | 2/2015 | Gilbert et al. |
| 8,974,134 B2 | 3/2015 | Wilson et al. |
| 9,205,447 B2 | 12/2015 | Wilson |
| 9,283,350 B2 | 3/2016 | Chappa et al. |
| 9,308,355 B2 | 4/2016 | Chappa et al. |
| 9,364,349 B2 | 6/2016 | Chappa et al. |
| 9,623,215 B2 | 4/2017 | Chappa et al. |
| 9,827,401 B2 * | 11/2017 | Chappa .............. B05B 13/0442 |
| 10,099,041 B2 | 10/2018 | Chappa et al. |
| 10,507,309 B2 | 12/2019 | Chappa et al. |
| 2001/0001824 A1 | 5/2001 | Wu |
| 2001/0014717 A1 | 8/2001 | Hossainy et al. |
| 2001/0022988 A1 | 9/2001 | Schwarz et al. |
| 2001/0026834 A1 | 10/2001 | Chappa et al. |
| 2001/0029351 A1 | 10/2001 | Falotico et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0013298 A1 | 1/2002 | Hunter |
| 2002/0018795 A1 | 2/2002 | Whitbourne et al. |
| 2002/0026176 A1 | 2/2002 | Varner et al. |
| 2002/0026236 A1 | 2/2002 | Helmus et al. |
| 2002/0032434 A1 | 3/2002 | Chudzik et al. |
| 2002/0032477 A1 | 3/2002 | Helmus et al. |
| 2002/0046521 A1 | 4/2002 | Steinacker, Sr. et al. |
| 2002/0051730 A1 | 5/2002 | Bodnar et al. |
| 2002/0054900 A1 | 5/2002 | Kamath et al. |
| 2002/0062730 A1 | 5/2002 | Thornton |
| 2002/0082679 A1 | 6/2002 | Sirhan et al. |
| 2002/0091433 A1 | 7/2002 | Ding et al. |
| 2002/0094440 A1 | 7/2002 | Llanos et al. |
| 2002/0103526 A1 | 8/2002 | Steinke |
| 2002/0107330 A1 | 8/2002 | Pinchuk et al. |
| 2002/0111590 A1 | 8/2002 | Davila et al. |
| 2002/0114823 A1 | 8/2002 | Sirhan et al. |
| 2002/0115400 A1 | 8/2002 | Skrmetta |
| 2002/0120326 A1 | 8/2002 | Michal |
| 2002/0133183 A1 | 9/2002 | Lentz et al. |
| 2002/0138048 A1 | 9/2002 | Tuch |
| 2002/0155212 A1 | 10/2002 | Hossainy |
| 2002/0159915 A1 | 10/2002 | Zelina et al. |
| 2002/0165265 A1 | 11/2002 | Hunter et al. |
| 2002/0168394 A1 | 11/2002 | Hossainy et al. |
| 2002/0188037 A1 | 12/2002 | Chudzik et al. |
| 2002/0188170 A1 | 12/2002 | Santamore et al. |
| 2002/0198511 A1 | 12/2002 | Varner et al. |
| 2003/0003221 A1 | 1/2003 | Zhong et al. |
| 2003/0004209 A1 | 1/2003 | Hunter et al. |
| 2003/0014036 A1 | 1/2003 | Varner et al. |
| 2003/0021828 A1 | 1/2003 | Guo et al. |
| 2003/0031780 A1 | 2/2003 | Chudzik et al. |
| 2003/0039689 A1 | 2/2003 | Chen et al. |
| 2003/0044514 A1 | 3/2003 | Richard |
| 2003/0054023 A1 | 3/2003 | Hughes et al. |
| 2003/0054090 A1 | 3/2003 | Hansen |
| 2003/0059520 A1 | 3/2003 | Chen et al. |
| 2003/0059920 A1 | 3/2003 | Drohan et al. |
| 2003/0060783 A1 | 3/2003 | Koole et al. |
| 2003/0065332 A1 | 4/2003 | Tenhuisen et al. |
| 2003/0083646 A1 | 5/2003 | Sirhan et al. |
| 2003/0088307 A1 | 5/2003 | Shulze et al. |
| 2003/0094736 A1 | 5/2003 | Qin et al. |
| 2003/0096131 A1 | 5/2003 | Beavers |
| 2003/0113439 A1 | 6/2003 | Pacetti et al. |
| 2003/0120200 A1 | 6/2003 | Bergheim et al. |
| 2003/0143315 A1 | 7/2003 | Pui et al. |
| 2003/0150380 A1 | 8/2003 | Yoe |
| 2003/0152693 A1 | 8/2003 | Su et al. |
| 2003/0157187 A1 | 8/2003 | Hunter |
| 2003/0157241 A1 | 8/2003 | Hossainy et al. |
| 2003/0158598 A1 | 8/2003 | Ashton et al. |
| 2003/0161937 A1 | 8/2003 | Leiby et al. |
| 2003/0165613 A1 | 9/2003 | Chappa et al. |
| 2003/0175324 A1 | 9/2003 | Robinson et al. |
| 2003/0181848 A1 | 9/2003 | Bergheim et al. |
| 2003/0190420 A1 | 10/2003 | Chappa et al. |
| 2003/0207856 A1 | 11/2003 | Tremble et al. |
| 2003/0215564 A1 | 11/2003 | Heller et al. |
| 2003/0229333 A1 | 12/2003 | Ashton et al. |
| 2003/0232087 A1 | 12/2003 | Lawin et al. |
| 2003/0232122 A1 | 12/2003 | Chappa et al. |
| 2003/0236513 A1 | 12/2003 | Schwarz et al. |
| 2003/0236514 A1 | 12/2003 | Schwarz |
| 2004/0006146 A1 | 1/2004 | Evans et al. |
| 2004/0022853 A1 | 2/2004 | Ashton et al. |
| 2004/0034357 A1 | 2/2004 | Beane et al. |
| 2004/0037886 A1 | 2/2004 | Hsu |
| 2004/0044404 A1 | 3/2004 | Stucke et al. |
| 2004/0047911 A1 | 3/2004 | Lyu et al. |
| 2004/0062592 A1 | 4/2004 | Shekalim et al. |

(56) References Cited

U.S. PATENT DOCUMENTS

| | | |
|---|---|---|
| 2004/0062875 A1 | 4/2004 | Chappa et al. |
| 2004/0073298 A1 | 4/2004 | Hossainy |
| 2004/0081745 A1 | 4/2004 | Hansen |
| 2004/0111818 A1 | 6/2004 | Ma |
| 2004/0121014 A1 | 6/2004 | Guo et al. |
| 2004/0133155 A1 | 7/2004 | Varner et al. |
| 2004/0137059 A1 | 7/2004 | Nivaggioli et al. |
| 2004/0142013 A1 | 7/2004 | Rubsamen |
| 2004/0143314 A1 | 7/2004 | Sommer et al. |
| 2004/0161547 A1 | 8/2004 | Carlson et al. |
| 2004/0185168 A1 | 9/2004 | Weber et al. |
| 2004/0194704 A1 | 10/2004 | Chappa et al. |
| 2004/0211362 A1 | 10/2004 | Castro et al. |
| 2004/0213893 A1 | 10/2004 | Boulais |
| 2005/0015142 A1 | 1/2005 | Austin et al. |
| 2005/0019371 A1 | 1/2005 | Anderson et al. |
| 2005/0059956 A1 | 3/2005 | Varner et al. |
| 2005/0098097 A1 | 5/2005 | Chen et al. |
| 2005/0129732 A1 | 6/2005 | Rubsamen |
| 2005/0142070 A1 | 6/2005 | Hartley |
| 2005/0143363 A1 | 6/2005 | De Juan et al. |
| 2005/0147690 A1 | 7/2005 | Masters et al. |
| 2005/0158449 A1 | 7/2005 | Chappa |
| 2005/0196518 A1 | 9/2005 | Stenzel et al. |
| 2005/0233061 A1 | 10/2005 | Schwarz et al. |
| 2005/0233062 A1 | 10/2005 | Hossainy et al. |
| 2005/0240147 A1 | 10/2005 | Makower et al. |
| 2005/0255142 A1 | 11/2005 | Chudzik et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0281863 A1 | 12/2005 | Anderson et al. |
| 2005/0287188 A1 | 12/2005 | Anderson et al. |
| 2006/0020295 A1 | 1/2006 | Brockway et al. |
| 2006/0029720 A1 | 2/2006 | Panos et al. |
| 2006/0045981 A1 | 3/2006 | Tsushi et al. |
| 2006/0059520 A1 | 3/2006 | Miyazawa et al. |
| 2006/0064134 A1 | 3/2006 | Mazar et al. |
| 2006/0064142 A1 | 3/2006 | Chavan et al. |
| 2006/0074404 A1 | 4/2006 | Struble |
| 2006/0088653 A1 | 4/2006 | Chappa |
| 2006/0096535 A1 | 5/2006 | Haller et al. |
| 2006/0110428 A1 | 5/2006 | De Juan et al. |
| 2006/0111754 A1 | 5/2006 | Rezai et al. |
| 2006/0116590 A1 | 6/2006 | Fayram et al. |
| 2006/0165872 A1 | 7/2006 | Chappa et al. |
| 2006/0191476 A1 | 8/2006 | Nagase et al. |
| 2006/0269663 A1 | 11/2006 | Mori et al. |
| 2007/0065481 A1 | 3/2007 | Chudzik et al. |
| 2007/0101933 A1 | 5/2007 | Chappa |
| 2007/0116855 A1 | 5/2007 | Fox et al. |
| 2007/0131165 A1 | 6/2007 | Fox et al. |
| 2007/0141232 A1 | 6/2007 | Tochterman et al. |
| 2007/0259100 A1 | 11/2007 | Guerriero et al. |
| 2007/0259102 A1 | 11/2007 | Mcniven et al. |
| 2007/0259125 A1 | 11/2007 | O'brien et al. |
| 2007/0275175 A1 | 11/2007 | Hossainy |
| 2008/0149025 A1 | 6/2008 | Swenson |
| 2008/0179781 A1 | 7/2008 | Iwata |
| 2008/0274266 A1 | 11/2008 | Davis et al. |
| 2009/0018643 A1 | 1/2009 | Hashi et al. |
| 2009/0054837 A1 | 2/2009 | Von Holst et al. |
| 2009/0084311 A1 | 4/2009 | Yoshida et al. |
| 2009/0090299 A1 | 4/2009 | Menendez et al. |
| 2009/0176030 A1 | 7/2009 | Carlson et al. |
| 2009/0269481 A1 | 10/2009 | Chappa et al. |
| 2009/0317537 A1 | 12/2009 | Andreacchi |
| 2010/0040766 A1 | 2/2010 | Chappa et al. |
| 2010/0055294 A1 | 3/2010 | Wang et al. |
| 2010/0070020 A1 | 3/2010 | Hashi et al. |
| 2010/0179475 A1 | 7/2010 | Hoffmann et al. |
| 2010/0227044 A1 | 9/2010 | Scheer |
| 2010/0272774 A1 | 10/2010 | Chappa |
| 2010/0319183 A1 | 12/2010 | Hulseman et al. |
| 2011/0046724 A1 | 2/2011 | Heilmann et al. |
| 2011/0104392 A1 | 5/2011 | Carlson et al. |
| 2011/0151199 A1 | 6/2011 | Nelson et al. |
| 2011/0238011 A1 | 9/2011 | Scheller et al. |
| 2011/0253170 A1 | 10/2011 | Clark et al. |
| 2011/0281019 A1 | 11/2011 | Gong et al. |
| 2011/0281020 A1 | 11/2011 | Gong et al. |
| 2011/0311713 A1 | 12/2011 | O'neill et al. |
| 2011/0311764 A1 | 12/2011 | Hulseman et al. |
| 2012/0025145 A1* | 2/2012 | Tokumoto ........... H01L 21/6715 252/500 |
| 2012/0043693 A1 | 2/2012 | King et al. |
| 2012/0059317 A1 | 3/2012 | Michiyo et al. |
| 2012/0100279 A1 | 4/2012 | Neumann et al. |
| 2012/0258246 A1 | 10/2012 | Saine et al. |
| 2012/0315376 A1 | 12/2012 | Nguyen et al. |
| 2013/0337147 A1 | 12/2013 | Chappa et al. |
| 2014/0121597 A1 | 5/2014 | Chappa et al. |
| 2014/0161964 A1 | 6/2014 | Chappa et al. |
| 2014/0328998 A1 | 11/2014 | Chappa et al. |
| 2015/0017429 A1 | 1/2015 | Li et al. |
| 2015/0044376 A1 | 2/2015 | Topf et al. |
| 2016/0256668 A1 | 9/2016 | Chappa et al. |
| 2016/0271644 A1 | 9/2016 | Weinmann et al. |
| 2018/0036519 A1 | 2/2018 | Chappa et al. |
| 2018/0110903 A1 | 4/2018 | Slager et al. |
| 2019/0099778 A1 | 4/2019 | Antoniazzi |
| 2019/0143661 A1 | 5/2019 | Hunt et al. |
| 2019/0151629 A1 | 5/2019 | Chappa et al. |
| 2020/0353502 A1* | 11/2020 | Ko ..................... B05B 13/0235 |
| 2020/0360572 A1 | 11/2020 | Militello et al. |

FOREIGN PATENT DOCUMENTS

| | | |
|---|---|---|
| DE | 20200223 | 4/2002 |
| DE | 10053826 | 5/2002 |
| EP | 0096433 | 12/1983 |
| EP | 0144873 | 6/1985 |
| EP | 0414233 | 2/1991 |
| EP | 0604022 | 6/1994 |
| EP | 0623354 | 11/1994 |
| EP | 0716836 | 6/1996 |
| EP | 0734721 | 10/1996 |
| EP | 0747069 | 12/1996 |
| EP | 0857516 | 2/1998 |
| EP | 0832655 | 4/1998 |
| EP | 0834282 | 4/1998 |
| EP | 0945148 | 9/1999 |
| EP | 0879595 | 1/2003 |
| EP | 1374924 | 1/2004 |
| EP | 1382302 | 1/2004 |
| EP | 1594623 | 4/2007 |
| EP | 0923953 | 8/2008 |
| EP | 1610836 | 8/2008 |
| EP | 2994241 | 3/2016 |
| EP | 3549679 | 10/2019 |
| FR | 1304457 | 8/1962 |
| FR | 2733163 | 10/1996 |
| GB | 525373 | 8/1940 |
| GB | 757659 | 9/1956 |
| GB | 2301296 | 12/1996 |
| GB | 104464 | 4/2001 |
| JP | 57048354 | 3/1982 |
| JP | 63-011547 | 1/1988 |
| JP | 02-036882 | 2/1990 |
| JP | H0262550 | 3/1990 |
| JP | H03021367 | 1/1991 |
| JP | 09-038546 | 2/1997 |
| JP | 09-194347 | 7/1997 |
| JP | 2003039015 | 2/2003 |
| JP | 2005059225 | 3/2005 |
| JP | 06-246207 | 9/2006 |
| JP | 08-086466 | 4/2008 |
| JP | 2015527092 | 9/2015 |
| JP | 2016504058 | 2/2016 |
| JP | 6445532 | 12/2018 |
| WO | 1989005664 | 6/1989 |
| WO | 1991012779 | 9/1991 |
| WO | 1992011895 | 7/1992 |
| WO | 1992015286 | 9/1992 |

(56) References Cited

FOREIGN PATENT DOCUMENTS

| | | |
|---|---|---|
| WO | 1993000174 | 1/1993 |
| WO | 1993015682 | 8/1993 |
| WO | 1994021308 | 9/1994 |
| WO | 1994021309 | 9/1994 |
| WO | 1995003036 | 2/1995 |
| WO | 1997010011 | 3/1997 |
| WO | 1997037640 | 11/1997 |
| WO | 1998017331 | 4/1998 |
| WO | 1998032474 | 7/1998 |
| WO | 1999001114 | 1/1999 |
| WO | 1998058690 | 3/1999 |
| WO | 1999036071 | 7/1999 |
| WO | 1999038546 | 8/1999 |
| WO | 1999055396 | 11/1999 |
| WO | 2000001322 | 1/2000 |
| WO | 2000002564 | 1/2000 |
| WO | 2000012163 | 3/2000 |
| WO | 2000021584 | 4/2000 |
| WO | 2001021326 | 3/2001 |
| WO | 2001032382 | 5/2001 |
| WO | 2001078626 | 10/2001 |
| WO | 2001094103 | 12/2001 |
| WO | 2002009786 | 2/2002 |
| WO | 2002020174 | 3/2002 |
| WO | 2003004072 | 1/2003 |
| WO | 2003024615 | 3/2003 |
| WO | 2004028579 | 4/2004 |
| WO | 2004028699 | 4/2004 |
| WO | 2004037126 | 5/2004 |
| WO | 2004037443 | 5/2004 |
| WO | 2004073885 | 9/2004 |
| WO | 2004091682 | 10/2004 |
| WO | 2004098565 | 11/2004 |
| WO | 2005009297 | 2/2005 |
| WO | 2006110366 | 10/2006 |
| WO | 2007059144 | 5/2007 |
| WO | 2007100801 | 9/2007 |
| WO | 2008002357 | 1/2008 |
| WO | 2009132214 | 10/2009 |
| WO | 2010024898 | 3/2010 |
| WO | 2010146096 | 12/2010 |
| WO | 2013181498 | 12/2013 |
| WO | 2014066760 | 5/2014 |
| WO | 2014182833 | 11/2014 |

OTHER PUBLICATIONS

"Communication Pursuant to Article 94(3) EPC," for European Patent Application No. 13729853.5 dated Apr. 30, 2018 (6 pages).
"Communication Pursuant to Article 94(3) EPC," for European Patent Application No. 13792526.9 dated Apr. 19, 2018 (5 pages).
"Communication Pursuant to Article 94(3) EPC," for European Patent Application No. 13792526.9 dated Aug. 6, 2019 (5 pages).
"Communication Pursuant to Article 94(3) EPC," for European Patent Application No. 13792526.9 dated Nov. 29, 2018 (4 pages).
"Communication Pursuant to Rule 164(2)(b) and Article 94(3) EPC," for European Patent Application No. 14730319.2 dated Sep. 4, 2017 (12 pages).
"Communication Pursuant to Rules 161 and 162 EPC," for European Patent Application No. 13729853.5, dated Feb. 13, 2015 (2 pages).
"Communication Pursuant to Rules 161(1) and 162 EPC," for European Application No. 13792526.9, dated Jul. 7, 2015 (2 pages).
"Communication Pursuant to Rules 161(1) and 162 EPC," for European Patent Application No. 14730319.2, dated Dec. 22, 2015 (2 pages).
"Complete File History," for U.S. Appl. No. 10/371,043 downloaded Jul. 8, 2015 (222 pages).
"Complete File History," for U.S. Appl. No. 10/409,434 downloaded Jul. 8, 2015 (199 pages).
"Complete File History," for U.S. Appl. No. 10/976,193, downloaded Jul. 8, 2015 (446 pages).
"Complete File History," for U.S. Appl. No. 10/976,348 downloaded Jul. 8, 2015 (219 pages).
"Complete File History," for U.S. Appl. No. 11/102,465 downloaded Jul. 8, 2015, (500 pages).
"Complete File History," for U.S. Appl. No. 11/375,487 downloaded Jul. 8, 2015 (301 pages).
"Complete File History," for U.S. Appl. No. 11/421,637 downloaded Jul. 8, 2015 (193 pages).
"Complete File History," for U.S. Appl. No. 11/539,443 downloaded Jul. 8, 2015, (269 pages).
"Complete File History," for U.S. Appl. No. 11/559,817 downloaded Jul. 8, 2015 (302 pages).
"Complete File History," for U.S. Appl. No. 11/823,055 downloaded Jul. 8, 2015, (156 pages).
"Complete File History," for U.S. Appl. No. 12/109,139 downloaded Dec. 18, 2017 (276 pages).
"Complete File History," for U.S. Appl. No. 12/980,920 downloaded Jul. 8, 2015 (141 pages).
"Complete File History," for U.S. Appl. No. 13/906,599 downloaded Dec. 18, 2017 (249 pages).
"Complete File History," for U.S. Appl. No. 14/063,124 downloaded Dec. 18, 2017 (174 pages).
"Complete File History," for U.S. Appl. No. 14/272,204 downloaded Dec. 18, 2017 (302 pages).
"Complete File History," for U.S. Appl. No. 15/061,234 downloaded Apr. 9, 2020 (118 pages).
"Complete File History," for U.S. Appl. No. 15/783,554 downloaded Apr. 9, 2020 (107 pages).
"Complete File History," for U.S. Appl. No. 16/160,425 downloaded Apr. 9, 2020 (131 pages).
"Cross-Link," http://en.wikipedia.org/wiki/Cross-link; retrieved Nov. 6, 2009 (4 pages).
Di Mario, et al., "Radioactive Stents—A Dead End?," Current Interventional Cardiology Reports, 2000 (2 pages), 87-88.
"European Examination Report," for European Application No. 04 711 809.6 dated Jan. 23, 2006 (4 pages).
"European Examination Report," for European Application No. 04 759 211.8 dated Aug. 7, 2006 (5 pages).
"European Examination Report," for European Application No. 06740366.7 dated Oct. 19, 2010 (4 pages).
"European Examination Report," for European Application No. 06740366.7, dated May 5, 2009 (4 pages).
"European Search Report," for European Patent Application No. 19174997.7 dated Sep. 10, 2019 (9 pages).
"Final Office Action," for Japanese Application No. 2006-509776, dated Jul. 5, 2011, (7 pages).
"Final Office Action," for Japanese Patent Application No. 2015-539837 dated Oct. 1, 2018 (7 pages) with English Translation.
"Final Rejection," for Japanese Patent Application No. 2015-515223 dated Nov. 22, 2017 (8 pages) with English translation.
"First Examination Report," for Costa Rican Patent Application No. 2014-0589 dated May 19, 2019 (2 pages) No English Translation.
"First Office Action," for CA Application No. 2604832, dated Mar. 16, 2012 (4 pages).
"First Office Action," for Japanese patent Application No. 2006-503609, dated Mar. 30, 2010 (7 pages) with English translation.
Hiemenz, Paul "Polymer Chemistry: The Basic Concepts," CRC Press, 1984 (pp. 9 and 12).
"International Preliminary Report on Patentability," for International Application No. PCT/US2005/038628 dated May 10, 2007 (10 pages).
"International Preliminary Report on Patentability," For PCT Application No. PCT/US2013/043547, dated Dec. 11, 2014 (7 pages).
"International Preliminary Report on Patentability," for PCT/US2013/066810, dated May 7, 2015 (12 pages).
"International Preliminary Report on Patentability," for PCT/US2014/037179 dated Nov. 19, 2015 (9 pages).
"International Preliminary Report on Patentability," from International Application No. PCT/US2004/004486, dated Aug. 19, 2005, (6 pages).
"International Search Report & Written Opinion," for PCT/US2004/010692, dated Jul. 23, 2004 (9 pages).

(56) References Cited

OTHER PUBLICATIONS

"International Search Report and Written Opinion," For International Application No. PCT/US2005/038628 dated Mar. 22, 2006 (16 pages).
"International Search Report and Written Opinion," For PCT Application No. PCT/US2014/037179 dated Feb. 19, 2015 (15 pages).
"International Search Report and Written Opinion," for PCT Application No. PCT/US2019/063311 dated Mar. 19, 2020 (13 pages).
"International Search Report and Written Opinion," for PCT/US2006/044218, dated Mar. 22, 2007 (12 pages).
"International Search Report and Written Opinion," for PCT/US2009/041575, dated Jul. 22, 2009 (15 pages).
"International Search Report and Written Opinion," for PCT/US2013/043547, dated Oct. 1, 2013 (10 pages).
"International Search Report and Written Opinion," for PCT/US2013/066810, dated Apr. 17, 2014 (18 pages).
"International Search Report," for PCT/US2004/004486, dated Jul. 19, 2004 (8 pages).
"Invitation to Pay Additional Fees and, Where Applicable, Protest Fee," for PCT/US2013/066810, dated Feb. 7, 2014 (6 pages).
"Invitation to Pay Additional Fees," For PCT Application No. PCT/US2014/037179, dated Oct. 24, 2014 (5 pages).
"Notice of Allowance Received," for Japanese Application No. 2006-509776, dated Dec. 1, 2011, (4 pages) including English translation.
"Office Action Response," for Canadian Patent Application No. 2,889,062 filed Mar. 9, 2020 (18 pages).
"Office Action," for Canadian Patent Application No. 2,874,824 dated Apr. 11, 2019 (5 pages).
"Office Action," for Canadian Patent Application No. 2,874,824 dated Jan. 9, 2020 (4 pages).
"Office Action," for Canadian Patent Application No. 2,889,062 dated Sep. 12, 2019 (3 pages).
"Office Action," for Japanese Patent Application No. 2015-515223 dated Feb. 21, 2019 (5 pages) with English Translation.
"Office Action," for Japanese Patent Application No. 2015-515223 dated Mar. 24, 2017 (10 pages) with English translation.
"Office Action," for Japanese Patent Application No. 2015-539837 dated Aug. 31, 2017 (11 pages) with English translation.
"Office Action," for Japanese Patent Application No. 2015-539837 dated Jun. 28, 2018 (7 pages) with English translation.
"Office Action," for Japanese Patent Application No. 2016-513047 dated Mar. 6, 2018 (11 pages) with English translation.
"Office Action," for Mexican Patent Application No. MX/a/2014/014574 dated Jun. 15, 2017 (1 page), English summary.
"Partial File History," for U.S. Appl. No. 14/063,113 downloaded Apr. 9, 2020 (409 pages).
"Pre-Appeal Examination Report," for Japanese Patent Application No. 2015-515223 dated Apr. 3, 2018 (5 pages).
"Pre-Appeal Examination Report," for Japanese Patent Application No. 2015-539837 dated Mar. 8, 2019 (2 pages), no translation available.
"Response to Communication Pursuant to Article 94(3) EPC," for European Patent Application No. 13729853.5, filed with the EPO Sep. 6, 2018 (12 pages).
"Response to Communication Pursuant to Article 94(3) EPC," for European Patent Application No. 13792526.9 filed Dec. 3, 2019 (9 pages).
"Response to Communication Pursuant to Article 94(3) EPC," for European Patent Application No. 13792526.9 filed Mar. 13, 2019 (6 pages).
"Response to Communication Pursuant to Article 94(3) EPC," for European Patent Application No. 13792526.9 filed with the EPO Aug. 17, 2018 (60 pages).
"Response to Communication Pursuant to Rule 164(2)(b) and Article 94(3) EPC," for European Patent Application No. 14730319.2 filed with the EPO Jan. 2, 2018 (19 pages).
"Response to Communication Pursuant to Rules 161 and 162 EPC," for European Patent Application No. 13729853.5, filed with the EPO Aug. 13, 2015 (21 pages).
"Response to Communication Pursuant to Rules 161 (1) and 162 EPC," for European Patent Application No. 13792526.9, dated Jul. 7, 2015 and filed with the EPO Jan. 7, 2016 (18 pages).
"Response to Communication Pursuant to Rules 161 (1) and 162 EPC," for European Patent Application No. 14730319.2, filed with the EPO Jun. 24, 2016 (11 pages).
"Response to European Examination Report," for European Application No. 06740366.7, filed Feb. 22, 2011 (8 pages).
"Response to Office Action," for Canadian Patent Application No. 2,874,824 filed Oct. 7, 2019 (18 pages).
"Response to Search Report," for European Patent Application No. 19174997.7 filed Mar. 31, 2020 (30 pages).
"Ultrasonic Spray Nozzle Systems," SONO-TEK Corporation Brochure, 2005 (16 pages).
Yeo, Yoon "A New Microencapsulation Method Using an Ultrasonic Atomizer Based on Interfacial Solvent Exchange," Journal of Controlled Release 100 (2004) pp. 379-388. 2004.
"International Preliminary Report on Patentability," for PCT Application No. PCT/US2019/063311 dated Jun. 10, 2021 (9 pages).

* cited by examiner

APPARATUS AND METHODS FOR COATING MEDICAL DEVICES

This application claims the benefit of U.S. Provisional Application No. 62/772,673, filed Nov. 29, 2018, the content of which is herein incorporated by reference in its entirety.

FIELD OF THE INVENTION

The present invention relates to apparatus and methods for coating medical devices.

BACKGROUND OF THE INVENTION

Functional improvements to implantable or insertable medical devices can be achieved by coating the surface of the device. For example, a coating formed on the surface of the device can provide improved lubricity, improved biocompatibility, or drug delivery properties to the surface. In turn, this can improve movement of the device in the body, extend the functional life of the device, or treat a medical condition near the site of implantation. However, various challenges exist for the design and use of coating apparatus designed to provide coatings to medical devices.

Traditional coating methods, such as dip coating, are often undesirable as they may result in flawed coatings that could compromise the function of the device or present problems during use. These methods can also result in coating inaccuracies, which can be manifested in variable amounts of the coated material being deposited on the surface of the device. When a drug is included in the coating material, it is often necessary to deliver precise amounts of the agent to the surface of the device to ensure that a subject receiving the coated device receives a proper dose of the agent. It has been difficult to achieve a great degree of accuracy using traditional coating methods and machines.

SUMMARY OF THE INVENTION

Embodiments of the invention include apparatus and methods for coating drug coated medical devices. In an embodiment, the invention includes a coating apparatus including a coating application unit. The coating application unit can include a fluid applicator having a lengthwise axis and a width. The fluid applicator can include a tip, the tip comprising a first face across the width of the fluid applicator. The first face of the fluid applicator can be oriented at an angle of from about 15 to about 75 degrees with respect to the lengthwise axis of the fluid applicator. The fluid applicator can define a second face intersecting the first face. The coating apparatus can further include a rotation mechanism and an axial motion mechanism. The axial motion mechanism can be configured to cause movement of at least one of the coating application unit and the rotation mechanism with respect to one another.

In an embodiment, a method of coating a medical device is included. The method can include rotating a medical device to be coated with a rotation mechanism. The method can further include contacting the surface of the medical device with a fluid applicator having a lengthwise axis and a width, the fluid applicator comprising a tip, the tip comprising a first face across the width of the fluid applicator. The first face can be oriented at an angle of from about 15 to about 75 degrees with respect to the lengthwise axis of the fluid applicator. The fluid applicator can define a second face intersecting the first face. The method can further include applying a coating solution onto the surface of the balloon with the fluid applicator.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Coatings are frequently applied onto the surfaces of various medical devices including, but not limited to, catheters and particularly balloon catheters. It is typically desirable for such coatings to be as uniform (in terms of thickness, composition, etc.) as possible. In some cases, the starting and/or stopping of a particular coating process (e.g., at the start of coating a particular device or when the coating for a particular device has been fully applied) can create challenges for forming a uniform coating. For example, during the coating process, a pool (or capillary pool) of coating materials may be associated with a direct-contact type coating applicator. This pool can help ensure desirable uniform coverage during the coating process. However, at the end of the process of coating a particular device, the coating applicator must be lifted from the surface of the medical device and some portion of the pool may be left behind on the surface. This can create an irregularity in the finished coating at the point where the coating tip is lifted from the surface unless additional processing steps are taken to remove it. In addition, this can result in the waste of materials in the coating solution, which may be extremely costly such as where the coating solution includes a costly active agent.

Embodiments herein can be used to apply uniform coatings, such as coatings including active agents, onto various medical devices, such as onto the balloons of drug coated or drug eluting balloon catheters, that have substantially uniform active agent concentrations along the length of the medical device. In addition, embodiments herein can minimize the amount of coating solution that is left on the medical device surface at the end of a coating cycle for enhanced coating uniformity and reduced waste. While not intending to be bound by theory, it is believed "double-bevel" or "double-face" coating applicators used with embodiments herein can enable the use of a smaller pool of coating materials during the coating process resulting in less excess material be left behind when the coating applicator is pulled up from the surface of the device being coated at the end of the coating cycle leading to enhanced coating uniformity and less coating solution waste.

Figure 1:
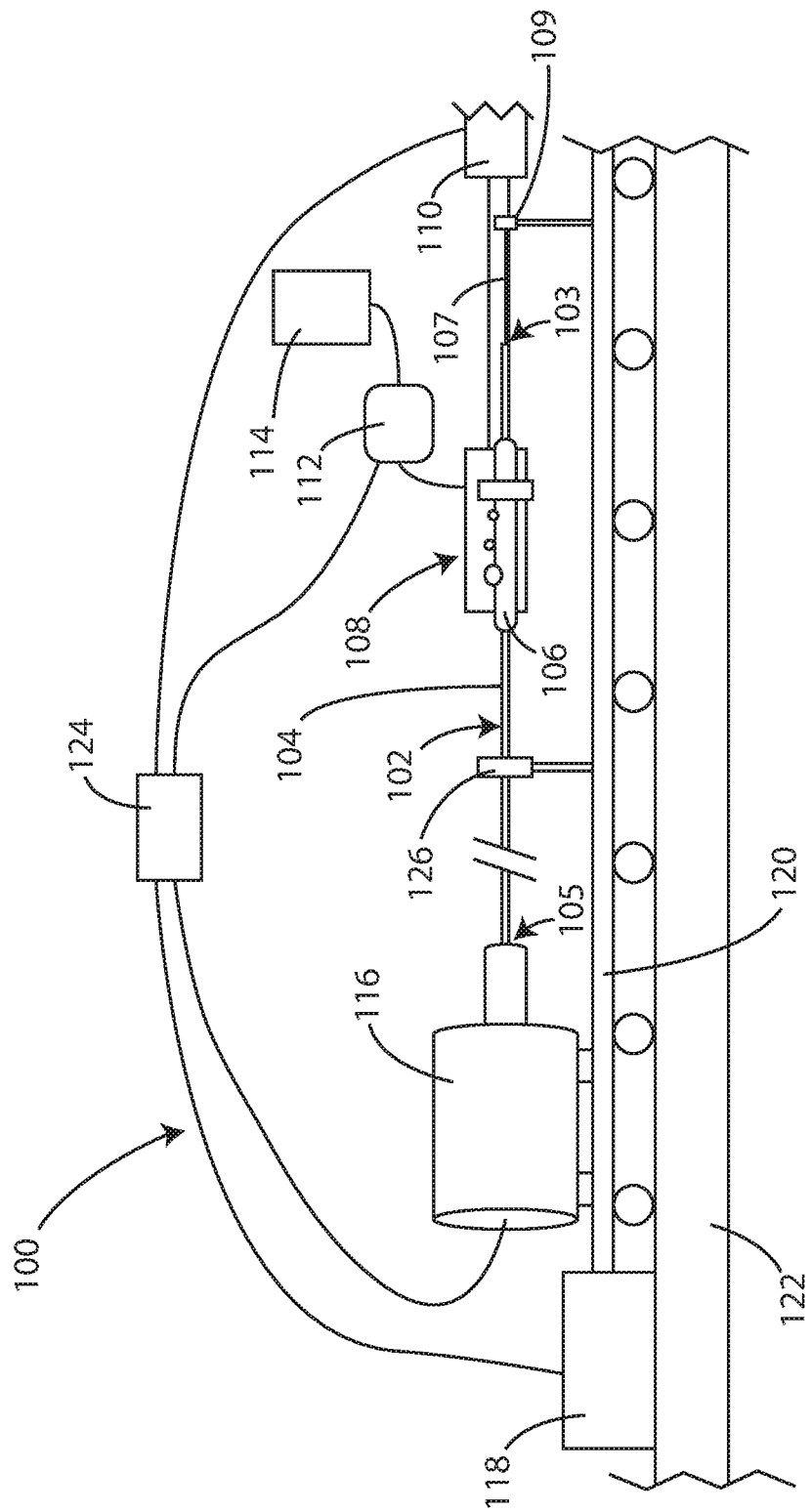
FIG. 1 is a schematic side view of a coating apparatus in accordance with various embodiments herein.

Referring now to FIG. 1, a schematic side view is shown of a coating apparatus 100 in accordance with various embodiments herein. The coating apparatus 100 is shown in conjunction with a medical device 102 (which could be a drug coated balloon catheter). In this example, the medical device 102 can include a catheter shaft 104 and a balloon 106. The balloon 106 can assume a deflated configuration and an inflated configuration. The medical device 102 can include a distal end 103 and a proximal end 105. The medical device 102 can include a proximal end manifold (not shown). The coating apparatus 100 can include a coating application unit 108. The coating apparatus 100 can further include, in some embodiments, an axial motion mechanism 110 (axial with respect to the axis of rotation of the balloon catheter and thus parallel to the lengthwise axis of the balloon catheter) that can function to move one or more components of the coating application unit 108. In some embodiments, axial motion can be substantially horizontal. In other embodiments, axial motion can be substantially vertical. In some embodiments, axial motion can be somewhere in between horizontal and vertical, depending on the orientation of the lengthwise axis of the balloon catheter. However, it will be appreciated that in other embodiments, the coating application unit 108 can remain stationary.

Coating of the balloon 106 to make it drug coated can occur starting at the proximal end of the balloon and proceeding to the distal end. However, in other embodiments, coating of the balloon 106 can occur starting at the distal end of the balloon and proceeding to the proximal end. In many embodiments, coating can take place with a single pass of the coating application unit 108 with respect to the balloon. However, in other embodiments, multiple passes of the coating application unit with respect to the balloon can be made.

The coating apparatus 100 can further include a fluid pump 112. The fluid pump 112 can be, for example, a syringe pump. The fluid pump 112 can be in fluid communication with components of the coating application unit 108 (such as the fluid applicator) and with a fluid reservoir 114. The fluid pump 112 can operate to pump a coating solution at a rate sufficient to apply about 0.5 µl to about 10 µl of the coating solution per millimeter of length of the balloon or other device to be coated. The coating apparatus 100 can further include a rotation mechanism 116 (or rotating balloon catheter fixture). The rotation mechanism 116 can be directly or indirectly coupled to the drug coated balloon catheter in order to rotate the medical device 102 around its lengthwise (major) axis (about the central lumen of the catheter). In some embodiments, the drug coated balloon catheter can be rotated at a speed of between 100 and 400 rotations per minute. In some embodiments, the drug coated balloon catheter can be rotated at a speed of between 200 and 300 rotations per minute.

In some embodiments, a guide wire 107, passing through the central lumen of the catheter, can extend from the distal tip of the catheter and be inserted into a distal tip support ring 109 or guide. In this manner, the guide wire 107 can be used to support the distal tip of the balloon catheter to be coated while allowing the balloon catheter to rotate freely.

The coating apparatus 100 can further include, in some embodiments, an axial motion mechanism 118 which can be configured to move the medical device 102 in the direction of its lengthwise major axis. In some embodiments, axial motion can be substantially horizontal. In other embodiments, axial motion can be substantially vertical. In some embodiments, axial motion can be somewhere in between horizontal and vertical, depending on the orientation of the lengthwise axis of the balloon catheter. In some embodiments, the axial motion mechanism 118 can be a linear actuator. In some embodiments, the axial motion mechanism 118 can include an electric motor.

The coating apparatus 100 can further include a frame member 120 (in some embodiments this can also be referred to as an axial motion support rail). The frame member 120 can support other components of the coating apparatus 100 such as one or more guides 126. The frame member 120 can itself be support by a platform 122. The coating apparatus 100 can further include a controller 124 that can serve to control operation of the coating apparatus 100 including, specifically, fluid pump 112, axial motion mechanism 110, rotation mechanism 116, and axial motion mechanism 118. Further aspects of coating apparatus components are described in U.S. Pat. No. 10,099,041, the content of which is herein incorporated by reference.

Figure 2:
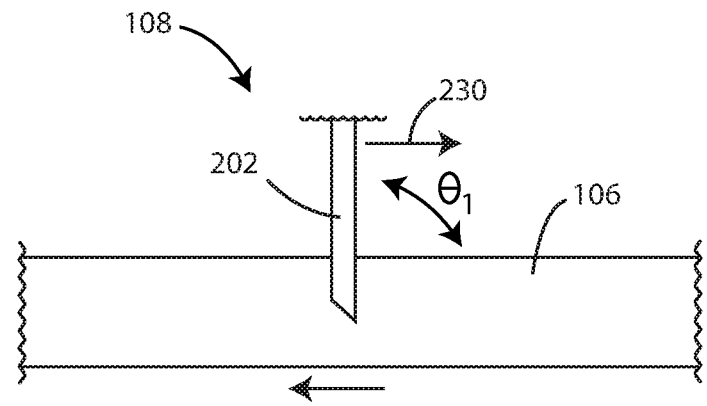
FIG. 2 is a schematic top view of a fluid applicator interfacing with a balloon catheter in accordance with various embodiments herein.

In various embodiments, the coating application unit can move, relative to the catheter or balloon. For example, referring now to FIG. 2, a schematic top view is shown of a fluid applicator (which can be part of a coating application unit 108) interfacing with a balloon catheter (as merely one example of device that can be coated) in accordance with various embodiments herein. In this embodiment, it can be seen that the fluid applicator 202 moves in the direction of arrow 230 relative to the balloon 106 (or catheter shaft 104). It will be appreciated, however, that this movement is relative in the sense that in some embodiments the fluid applicator can move and the balloon can be stationary (or rotating, but stationary along its longitudinal axis), in some embodiments, the balloon can move (such as along its longitudinal axis) and the fluid applicator can be stationary, and in some embodiments both the balloon and the fluid applicator can move. The speed of movement of the device to be coated relative to the coating application unit can vary depending on the amount of coating solution to be applied. In some embodiments the speed can be from about 0.02 centimeters per second to about 0.2 centimeters per second.

It will be appreciated that based on the rotation of the drug coated balloon catheter and the movement of the balloon relative to the coating application unit that the path of the deposition of the coating onto the balloon follows a roughly helical path. It will be appreciated that the combination of the rotation speed of the drug coated balloon catheter and the speed of the movement of the balloon relative to the coating application unit can influence the amount of coating solution that is deposited at any given point and the nature of the helical path. For example, the coating material can be deposited in helical layers that partially overlap one another at their edges, helical layers wherein the edge of one turn substantially meets the edge of a previous turn, and helical layers wherein there are gaps in between subsequent helical turns. In some embodiments, these helical patterns can be configured so as to maximize release of the active agent. For example, in some embodiments, the apparatus can be used to coat device so as to produce helical ridges of the coating material on the balloon surface.

The fluid applicator 202 can be disposed at a particular angle ($\Theta_1$) with respect to the balloon 106 (or catheter shaft 104 or other medical device component). In some embodiments, $\Theta_1$ can be from about 30 degrees to about 150 degrees, or about 45 degrees to about 135 degrees, or from about 60 degrees to about 120 degrees, or from about 75 degrees to about 105 degrees, or from about 85 degrees to about 95 degrees, or in some embodiments about 90 degrees.

Figure 3:
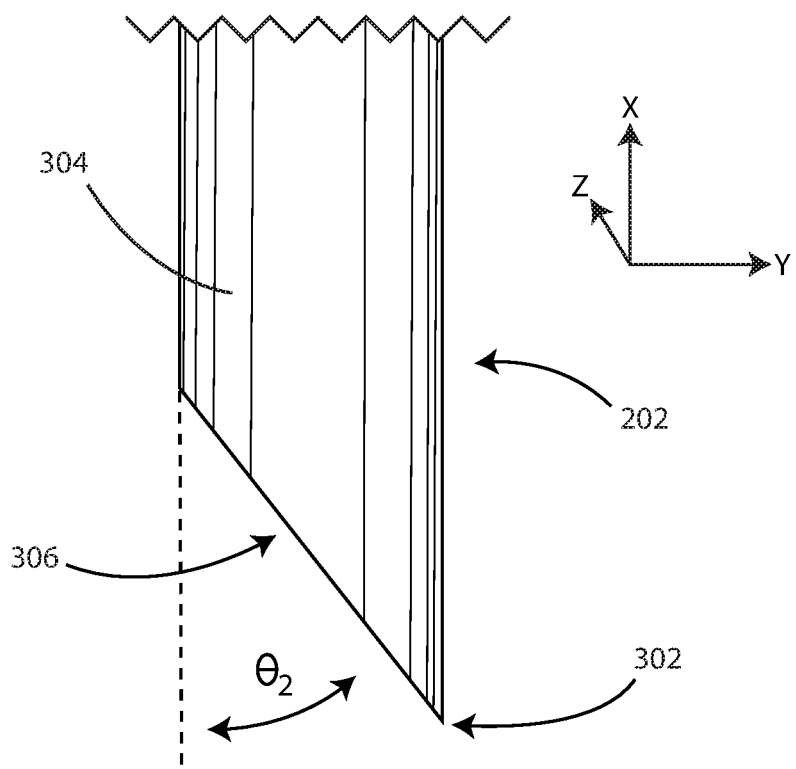
FIG. 3 is a schematic top view of a fluid applicator in accordance with various embodiments herein.

Referring now to FIG. 3, a schematic top view is shown of a fluid applicator 202 in accordance with various embodiments herein. The fluid applicator 202 includes a tip area 302 and a shaft 304. The fluid applicator 202 can include a tip area 302 having a first face 306 (or beveled surface) that is angled with respect to the lengthwise axis of the fluid applicator 202. The first face 306 can extend all the way across the width of the fluid applicator 202 in some embodiments. In some embodiments, the first face 306 can have an angle $\Theta_2$ with respect to a line parallel to the lengthwise axis of the fluid applicator 202. In some embodiments, angle $\Theta_2$ can be from about 10 to about 80 degrees. In some embodiments, angle $\Theta_2$ can be from about 25 to about 65 degrees. In some embodiments, angle $\Theta_2$ can be from about 35 to about 55 degrees. In some embodiments, angle $\Theta_2$ can be from about 40 to about 50 degrees. In some embodiments, angle $\Theta_2$ can be about 45 degrees. The first face 306 can be referred to as a first bevel, such as in the context of reference to dual bevel fluid applicators and systems herein.

In some embodiments, the shaft 304 of the fluid applicator can be made of a material that flexes. For example, the shaft 304 can, in some embodiments, be sufficient flexible such that it can move in the Z-axis direction by about 0.5 to about 4 mm, or from about 1 to 2 mm. In some embodiments, the shaft 304 can be about 0.5 to 5 centimeters, or from about 1 to 2 centimeters in length or can span an equal distance before connecting to another structure that is part of the coating apparatus. Movement in the Z-axis direction (through flexing or movement enabled by a separate structure connected to the shaft such as a pivoting mount) can be significant for purposes of maintaining continuity of contact between the fluid applicator and the surface of the device to be coated. In some embodiments, the shaft 304 of the fluid applicator can be positioned such that it exerts a small degree of pressure against the surface of the medical device such that when an irregularity in the surface of the medical device is encountered the fluid applicator can move slightly in order to maintain contact with the balloon surface.

In some embodiments, the shaft 304 of the fluid applicator can be formed of a translucent or transparent material. In other embodiments, the shaft 304 can be substantially opaque.

Exemplary materials for the shaft 304 of the fluid applicator can include, but are not limited to, polymers such as ethylene vinyl acetate (EVA), fluoropolymers (such as PTFE and PVDF), polyamides, polycarbonate, polystyrene, polyolefins (such as polyethylene and polypropylene), polyketones, polyurethane, polyvinylchloride, and the like. Other materials beyond polymers can also be used including, but not limited to, metals, glasses, composites, and the like.

In various embodiments, the shaft 304 can be made from a tubing material of about 16 gauge to 22 gauge, or about 20 gauge, which corresponds to a wall thickness of about 0.035 inches (or 0.889 mm). In cross-section, the shaft 304 can be circular, oval, polygonal, or the like.

Figure 4:
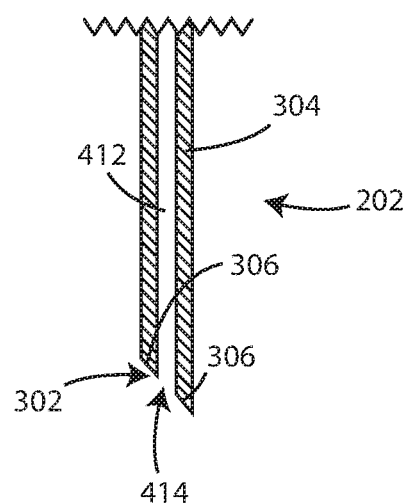
FIG. 4 is a schematic cross-sectional view of a fluid applicator in accordance with various embodiments herein.

Referring now to FIG. 4, a schematic cross-sectional view is shown of a fluid applicator 202 in accordance with various embodiments herein. The fluid applicator defines a central channel 412 through which a fluid coating composition can flow before exiting the tip through an orifice 414 (or aperture) which can be at least partly within the first face 306. The diameter of the central channel 412 (or inner diameter of the shaft 304) can be from about 1000 microns to about 1000 microns, or from about 500 microns to about 200 microns.

Figure 5:
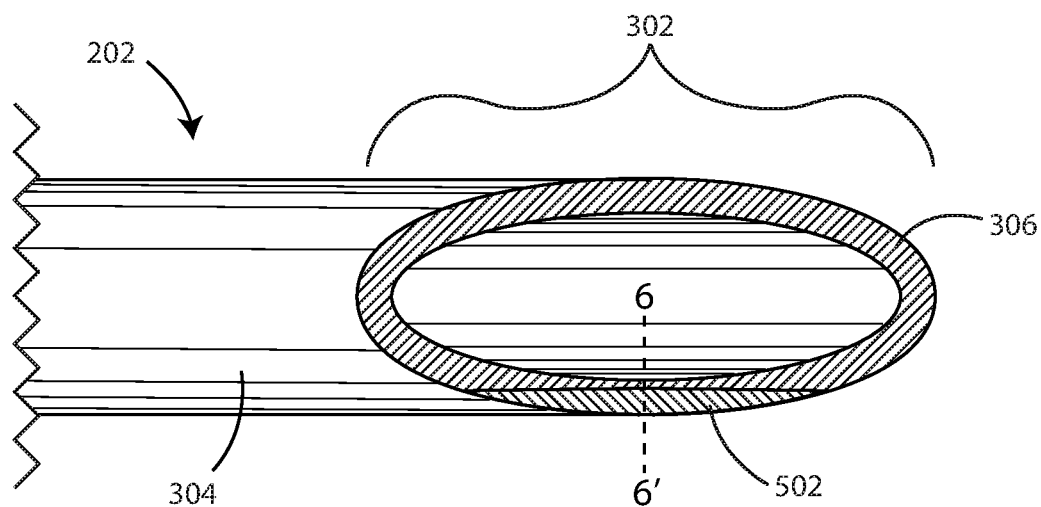
FIG. 5 is a schematic side view is shown of a portion of a fluid applicator 202 in accordance with various embodiments herein.

In various embodiments herein, the fluid applicator 202 can include a tip area 302 that includes a second face (or additional contact surface or second bevel). Referring now to FIG. 5, a schematic side view is shown of a portion of a fluid applicator 202 in accordance with various embodiments herein. A second face 502 (or second contact surface or second bevel) can intersect the first face 306 at a bottom portion thereof. In some embodiments, the second face 502 is curved. In some embodiments, the second face 502 is concave. In some embodiments, the second face 502 can intersect the first face 306 at a sharp angle. In other embodiments, the second face 502 can intersect the first face 306 with a rounded transition between the two.

In some embodiments, the second face 502 intersects the first face at a position lower than half the total height of the first face 306. In some embodiments, the second face 502 slopes inward from the first face 306. In some embodiments, the second face 502 has a surface area that is less than 50% of the surface area of the first face 306 across the width of the fluid applicator. In some embodiments, the second face 502 has a length that is less than the length of the first face 306 across the width of the fluid applicator.

Figure 6:
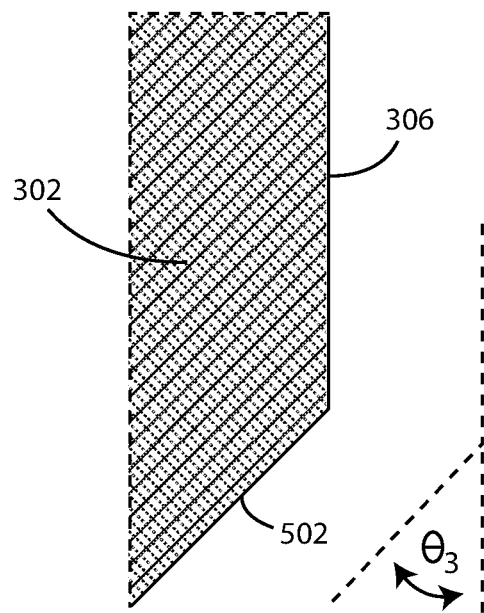
FIG. 6 is a schematic cross-sectional view of a portion of a tip area of a fluid applicator as taken along line 6-6' of FIG. 5 in accordance with various embodiments herein.

Referring now to FIG. 6, a cross-sectional view is shown of a portion of the tip area 302 of a fluid applicator 202 as taken along line 6-6' of FIG. 5 showing the interface between the first face 306 or first bevel and the second face 502 or second bevel. The second face 502 or second bevel can intersect the first face 306 or first bevel at a particular angle $\Theta_3$ that can from about 15 to about 90 degrees, or about 30 to about 85 degrees, or about 45 to about 85 degrees, or about 60 to about 85 degrees.

Figure 7:
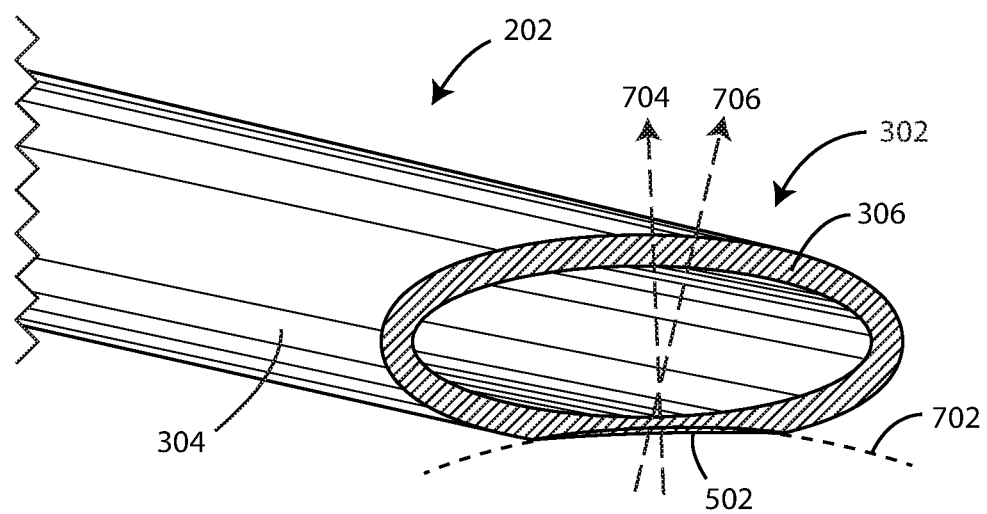
FIG. 7 is a schematic perspective view of a portion of a fluid applicator in accordance with various embodiments herein.

In some embodiments, the second face 502 can be substantially flat or planar. In other embodiments, the second face 502 can exhibit a degree of curvature. In some embodiments, the second face 502 can be concave. Referring now to FIG. 7, a schematic perspective view is shown of a portion of a fluid applicator 202 in accordance with various embodiments herein. In this view, it can be seen that the second face 502 follows a curve 702 that is concave with respect to the bottom of the first face 306. The specific radius of curvature can vary. In some embodiments, the radius of curvature can be equal to that of a sphere having an outer diameter of about 3, 4, 5, 6, 7, 8, 9, 10, 11, 12, 14, or 16 mm, or an amount falling within a range between any of the foregoing.

In some embodiments, the second face 502 can be aligned squarely with the first face 306. For example, where the second face 502 is curved, the direction of the apex of the curve can be aligned with arrow 704, or directly perpendicular to the first face 306. However, in some embodiments, the second face can be aligned differently. For example, in some embodiments, the second face can be aligned such that the direction of the apex of the curve can be aligned with arrow 706, or directly perpendicular to the shaft 304. In various embodiments, the second face can be aligned such that the direction of the apex of the curve is aligned in a direction between arrows 704 and 706.

Figure 8:
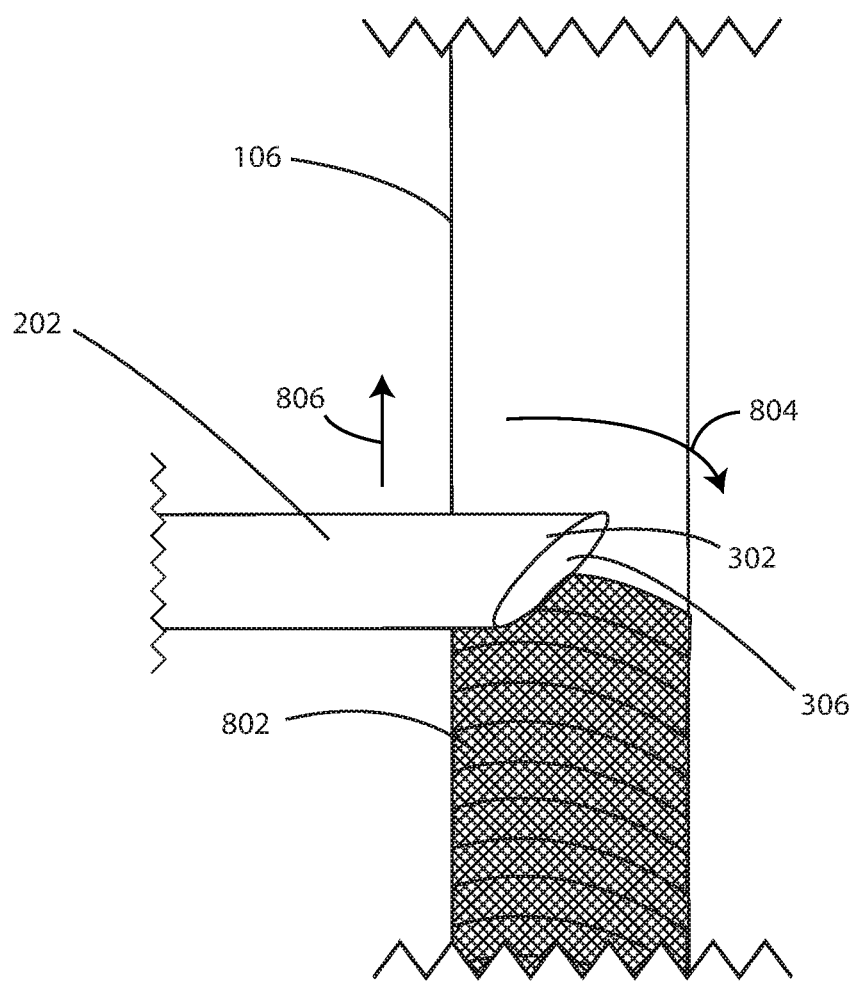
FIG. 8 is a schematic view of a fluid applicator in the process of depositing a coating onto a medical device in accordance with various embodiments herein.

The coating can be deposited in various ways using the fluid applicator. In some embodiments, the device-to-be-coated can rotate while the fluid application is in contact with a surface thereof and the coating solution can be pumped out of the fluid application. Referring now to FIG. 8, a schematic view is shown of a fluid applicator 202 in the process of depositing a coating 802 onto a balloon 106. The balloon 106 can rotate in the direction of arrow 804. The first face 306 can be disposed on the tip area 302 of the fluid applicator 202. A coating material solution can come out of the first face 306 and be deposited onto the surface of the balloon 106. The fluid applicator 202 can move in the direction of arrow 806 relative to the balloon 106.

Figure 9:
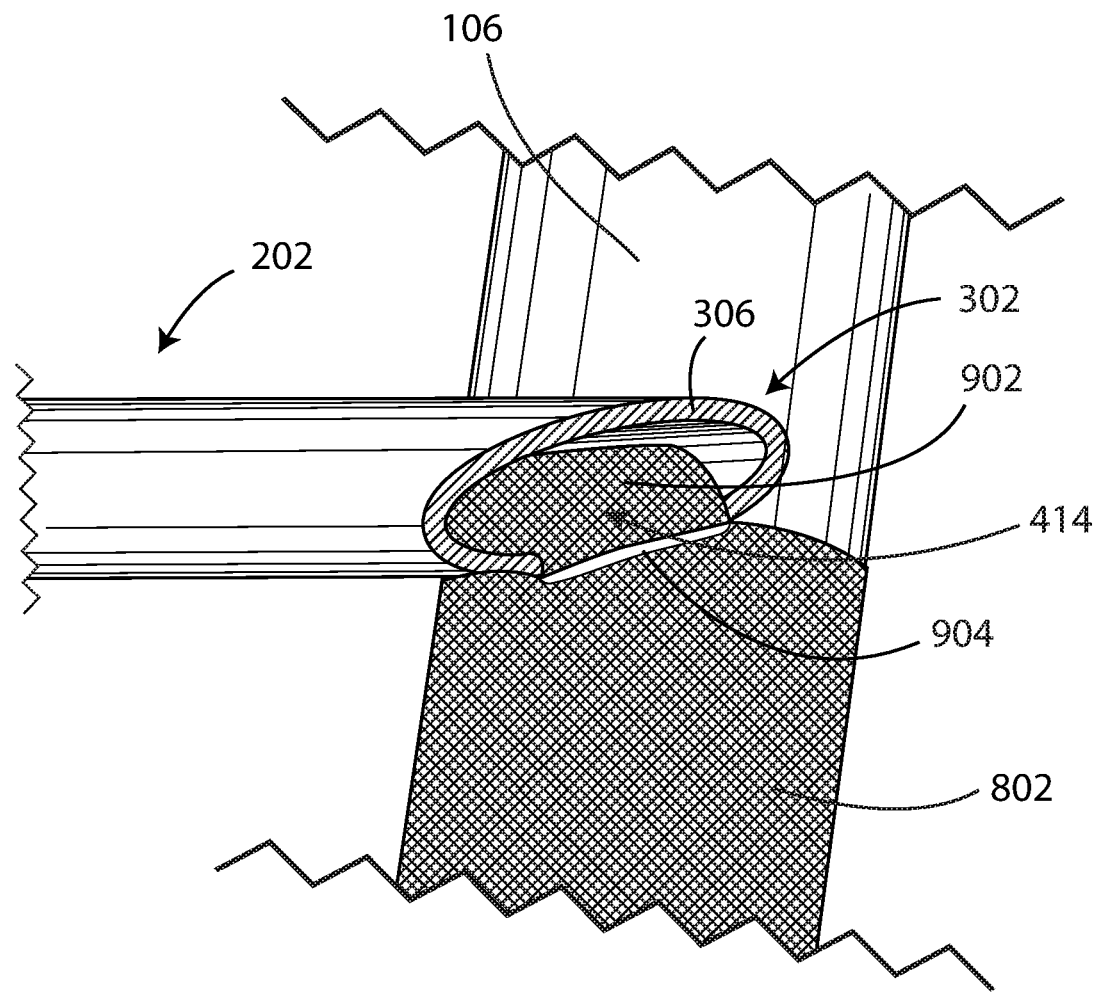
FIG. 9 is a schematic perspective view of a coating being applied to a medical device surface in accordance with various embodiments herein.

In various embodiments herein, the "double-bevel" or "double-face" coating applicators used with embodiments herein can enable the use of a smaller pool of coating materials during the coating process resulting in less excess material being left behind when the coating tip is pulled up from the surface of the device being coated at the end of the coating cycle. This can lead to enhanced coating uniformity and less coating solution waste. Referring now to FIG. 9, a schematic perspective view is shown of a coating 802 being applied to a balloon 106 surface in accordance with various embodiments herein. A fluid coating solution 902 can pass out of an orifice 414 in the first face 306, wherein the first face 306 is disposed on the tip area 302 of the fluid applicator 202. A pool (or capillary pool) of coating solution 904 can be present in the area near where the tip area 302 interfaces with the balloon 106. The second face (not visible in this view) can enable the use of a smaller pool of coating solution 904 than may otherwise be present with an otherwise similar fluid applicator missing the second face.

While many solution applicators described herein have been shown with body members that are substantially uniform in diameter (such as a tubular shape), it will be appreciated that other shapes are also contemplated herein. By way of example, in some embodiments a fluid applicator with a conical shape can be used.

Figure 10:
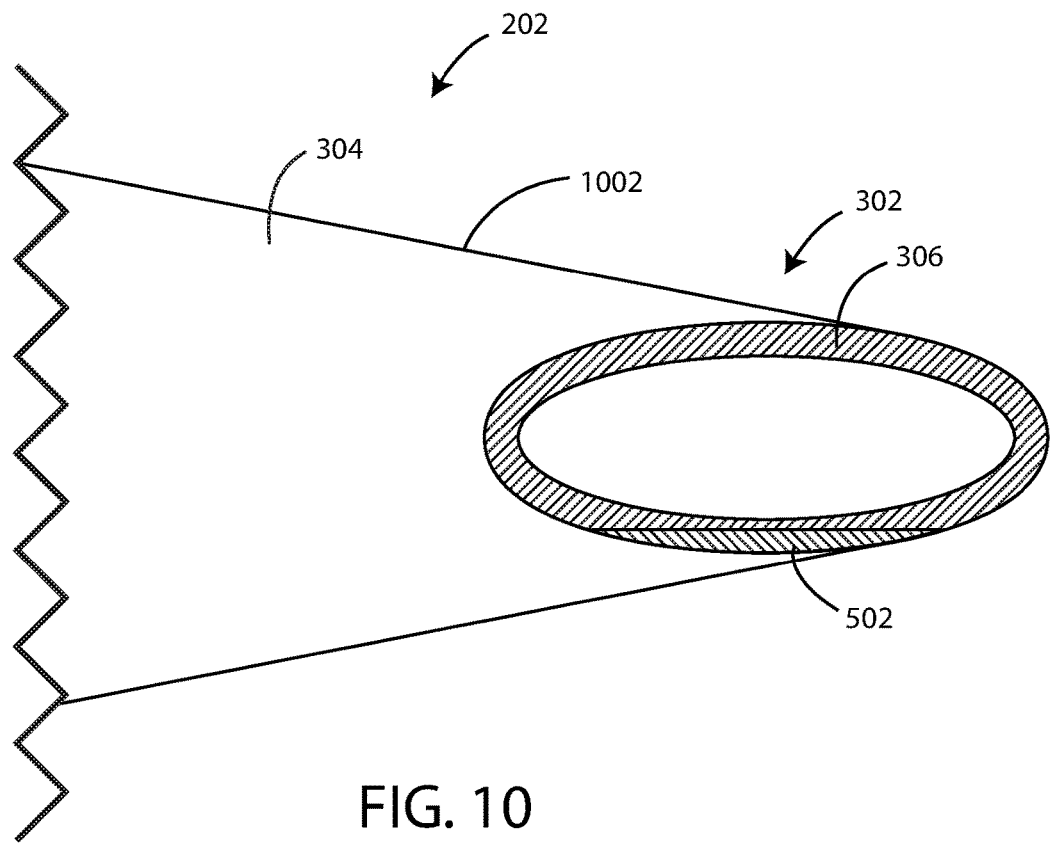
FIG. 10 is a schematic view of a fluid applicator with a conical body in accordance with various embodiments herein.

Referring now to FIG. 10, a schematic view is shown of a fluid applicator 202 with a shaft 304 that is conical in accordance with various embodiments herein. The shaft 304 can include a conical surface 1002. The fluid applicator 202 can include a tip area 302 including a first face 306 and a second face 502.

Medical Devices

It will be appreciated that many different medical devices can be coated using equipment and methods herein. In various embodiments, rotatable medical device can be coated using equipment and methods described herein. In various embodiments, relatively long medical devices (such as those having a length that it is at least 20 times their diameter) can be coated using equipment and methods described herein.

One type of medical device is a balloon catheter. Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. Balloon catheters generally include four portions, the balloon, catheter shaft, guide wire, and manifold. A balloon catheter generally includes an elongated catheter shaft with an inflatable balloon attached to a distal section of the catheter shaft. At a proximal end of the catheter shaft, there is typically a manifold. At the manifold end, placement of the catheter can be facilitated using a guide wire. Guide wires are small and maneuverable when inserted into an artery. Once the guide wire is moved to the target location, the catheter with balloon portion is then fed over the guide wire until the balloon reaches the target location in the vessel. The balloon is typically inserted into the arterial lumen of a patient and advanced through the lumen in an unexpanded state. The balloon is then inflated when the catheter reaches target site resulting in application of mechanical force sufficient to cause vessel dilation. The balloon is typically inflated using a fluid, which is injected through an inflation port. The manifold can control the fluid introduction within shaft for expansion of the balloon. The mechanics of fluid transfer and introduction within balloons vary according to the specific design of the catheter, and are well known in the art.

Figure 11:
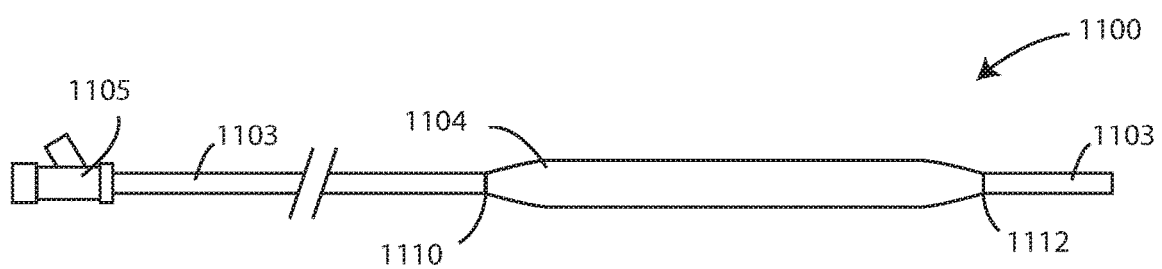
FIG. 11 is a schematic view of a medical device in accordance with various embodiments herein.

Referring now to FIG. 11, a schematic view of a medical device 1100 is shown. The medical device 1100 can optionally include a connection manifold 1105, a shaft 1103 having a surface, and an expandable portion 1104 (such as a balloon) having a surface. The expandable portion 1104 can include a proximal end 1110 and a distal end 1112. Coating segments can be disposed onto one or more of the shaft 1103 and the expandable portion 1104. In some embodiments, the expandable portion 1104 can include multiple coating segments thereon disposed adjacently to one another.

Coating Solutions

It will be appreciated that coating solutions applied onto medical devices herein can include various components including, but not limited to, one or more active agents, carrier agents and/or solvents, polymers (including degradable or non-degradable polymers), cross-linking agents, excipients, and the like. The relative amounts of the components of the coating solution will depend on various factors including the desired amount of active agent to be applied to the balloon and the desired release rate of the active agent. Exemplary coating compositions are described in U.S. Publ. Pat. Appl. No. 2018/0110903, the content of which is herein incorporated by reference. Exemplary cross-linking agents are described in U.S. Pat. No. 8,889,760, the content of which is herein incorporated by reference.

In some embodiments, active agents can specifically include those wherein the coating solution is the form of a suspension or emulsion including active agent particles.

Methods

In various embodiments, a method of coating a medical device is included. The method can include rotating a medical device to be coated with a rotation mechanism. Rotation can be performed at various speeds such as 20, 50, 100, 150, 200, 300, 400, 500, 600, 800 or 1000 RPM or more, or a speed falling within a range between any of the foregoing. The method can include contacting the surface of the medical device with a fluid applicator having a lengthwise axis and a width. The fluid applicator can have a tip, the tip comprising a first face across the width of the fluid applicator. The first face can be oriented at an angle of from about 15 to about 75 degrees with respect to the lengthwise axis of the fluid applicator, wherein the fluid applicator defines a second face intersecting the first face. The method can include applying a coating solution onto the surface of the balloon with the fluid applicator. In some embodiments, the second face is curved. In some embodiments, the second face is concave. In some embodiments, the second face intersects the first face at an angle of about 15 to 75 degrees. In some embodiments, the second face intersects the first face at a position lower than half the total height of the first face. In some embodiments, the fluid applicator can include a polymeric tube defining a central channel for passage of a fluid therethrough. In some embodiments, the fluid applicator can be in fluid communication with a fluid supply pump. In some embodiments, the second face slopes inward from the first face. In some embodiments, the second face has a surface area that is less than 50% of the surface area of the first face across the width of the fluid applicator. In some embodiments, the second face has a length that is less than the length of the first face across the width of the fluid applicator.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. A coating apparatus comprising:
   a coating application unit comprising
      a fluid applicator having a lengthwise axis and a width, the fluid applicator comprising a tip, the tip comprising a first face across the width of the fluid applicator, the first face oriented at an angle of from about 15 to about 75 degrees with respect to the lengthwise axis of the fluid applicator,
      wherein the fluid applicator defines a second face intersecting the first face, wherein the second face is configured to contact a surface of a device to be coated while the fluid applicator applies a coating to the device, wherein the second face is curved and concave;
   a rotation mechanism; and
   an axial motion mechanism, the axial motion mechanism configured to cause movement of at least one of the coating application unit and the rotation mechanism with respect to one another.

2. The coating apparatus of claim 1, wherein the second face intersects the first face at an angle of about 15 to 90 degrees.

3. The coating apparatus of claim 1, wherein the second face intersects the first face at a position lower than half the total height of the first face.

4. The coating apparatus of claim 1, the fluid applicator comprising a polymeric tube defining a central channel for passage of a fluid therethrough.

5. The coating apparatus of claim 1, the fluid applicator in fluid communication with a fluid supply pump.

6. The coating apparatus of claim 1, wherein the second face slopes inward from the first face.

7. The coating apparatus of claim 1, wherein the second face has a surface area that is less than 50% of the surface area of the first face across the width of the fluid applicator.

8. The coating apparatus of claim 1, wherein the second face has a length that is less than the length of the first face across the width of the fluid applicator.

9. A coating apparatus comprising:
   a coating application unit comprising
      a fluid applicator having a lengthwise axis and a width, the fluid applicator comprising a tip, the tip comprising a first face across the width of the fluid applicator, the first face oriented at an angle of from about 15 to about 75 degrees with respect to the lengthwise axis of the fluid applicator,
      wherein the fluid applicator defines a second face intersecting the first face, wherein the second face is oriented at an oblique angle relative to the lengthwise axis of the fluid applicator, wherein the second face is configured to contact a surface of a device to be coated while the fluid applicator applies a coating to the device, wherein the second face is concave;
   a rotation mechanism configured to rotate the device about a rotation axis; and
   an axial motion mechanism, the axial motion mechanism configured to cause movement of at least one of the coating application unit and the rotation mechanism with respect to one another about an axis parallel to the rotation axis.

10. A coating apparatus comprising:
    a coating application unit comprising
       a fluid applicator having a lengthwise axis and a width, the fluid applicator comprising a tip, the tip comprising a first face across the width of the fluid applicator, the first face oriented at an angle of from about 15 to about 75 degrees with respect to the lengthwise axis of the fluid applicator, wherein the fluid applicator defines a second face intersecting the first face, wherein the second face is configured to contact a surface of a device to be coated while the fluid applicator applies a coating to the device, a rotation mechanism configured to rotate a device about a rotation axis that is substantially orthogonal to the lengthwise axis of the fluid applicator, wherein the second face is concave; and an axial motion mechanism, the axial motion mechanism configured to cause movement of at least one of the coating application unit and the rotation mechanism with respect to one another.

11. The coating apparatus of claim 10, wherein the rotation mechanism is configured to rotate the part about a lengthwise axis of the part.

12. The coating apparatus of claim 10, wherein the fluid applicator is configured to remain stationary.

13. The coating apparatus of claim 10, wherein the fluid applicator is configured to contact a surface of the part.

14. The coating apparatus of claim 10, wherein the part is a balloon catheter.

* * * * *